United States Patent [19]

Calabrese et al.

[11] Patent Number: 5,437,684
[45] Date of Patent: Aug. 1, 1995

[54] CIRCULAR ANASTOMOSIS DEVICE

[75] Inventors: Philip D. Calabrese, Danbury; Frank J. Viola, Sandy Hook; Stephen W. Gerry, Bethel, all of Conn.

[73] Assignee: United States Surgical Corporation, Norwalk, Conn.

[21] Appl. No.: 130,230

[22] Filed: Oct. 1, 1993

[51] Int. Cl.$^6$ .............................................. A61B 17/00
[52] U.S. Cl. ................... 606/153; 606/151; 227/175; 227/179; 227/19
[58] Field of Search ............... 606/142, 143, 151, 153, 606/213, 215; 227/175–181, 19, 901

[56] References Cited

U.S. PATENT DOCUMENTS

| | | | |
|---|---|---|---|
| 4,027,510 | 6/1977 | Hiltebrandt . | |
| 4,104,905 | 8/1978 | Zachary | 73/40 |
| 4,316,624 | 2/1982 | Davlin | 285/158 |
| 4,485,817 | 12/1984 | Swiggett | 227/180 |
| 4,576,167 | 3/1986 | Noiles . | |
| 4,796,899 | 1/1989 | Herrick et al. | 277/228 |
| 4,843,835 | 7/1989 | Goetz et al. | 62/285 |
| 5,005,749 | 4/1991 | Aranyi . | |
| 5,040,715 | 8/1991 | Green et al. . | |
| 5,076,188 | 12/1991 | Burroughs | 114/201 |
| 5,084,057 | 1/1992 | Green et al. . | |
| 5,100,420 | 3/1992 | Green et al. . | |
| 5,112,343 | 5/1992 | Thornton | 606/142 |
| 5,119,983 | 6/1992 | Green et al. . | |
| 5,125,553 | 6/1992 | Oddsen et al. . | |
| 5,158,222 | 10/1992 | Green et al. . | |
| 5,171,249 | 12/1992 | Stefanchik et al. . | |
| 5,197,649 | 3/1993 | Bessler et al. | 227/179 |
| 5,254,116 | 10/1993 | Baust et al. | 606/23 |
| 5,291,974 | 3/1994 | Bianchi | 188/322.17 |
| 5,312,023 | 5/1994 | Green et al. | 227/175 |
| 5,333,773 | 8/1994 | Main et al. . | |
| 5,364,001 | 11/1994 | Bryan . | |
| 5,364,002 | 11/1994 | Green et al. . | |

Primary Examiner—Peter A. Aschenbrenner
Assistant Examiner—Jeffrey A. Schmidt

[57] ABSTRACT

A surgical instrument for performing a circular anastomosis is disclosed. The instrument is provided with three seals to permit use during endoscopic procedures. The first seal is configured and dimensioned to at least partially contact an outer portion of a compression member and an inner portion of an outer tube. The second seal is disposed about the compression member and is located proximal of the first seal. The third seal disposed about an elongate member, is located proximal of the second seal and is fabricated from polyethylene foam.

6 Claims, 2 Drawing Sheets

CIRCULAR ANASTOMOSIS DEVICE

BACKGROUND OF THE INVENTION

1. Field of the Invention

The present invention relates to surgical instruments for applying surgical staples to body tissue, and more particularly to a sealed apparatus for applying an annular array of surgical staples.

2. Discussion of the Related Art

Surgical stapling devices for applying an annular array of staples to tissue are well known in the art. These devices typically include a stapling assembly and an anvil member at the distal end of the apparatus. The stapling assembly generally includes a circular array of staples and means for expelling the staples against the anvil member. The anvil member typically includes means for completing the circular anastomosis, i.e. an array of bucket-shaped members against which the staples are formed after being expelled from the stapling assembly.

Surgical stapling devices for applying an annular array of staples are well known in gastric and esophageal surgery, for example, in classic or modified gastric reconstruction typically formed in an end-to-end, end-to-side or side-to-side manner. One such instrument is the Premium CEEA ® surgical stapler, manufactured and sold by United States Surgical Corporation. In use, the instrument typically is positioned within the lumen of an organ such as the stomach, esophagus or intestine in order to perform the anastomosis. The tissue is positioned between the anvil and the stapling assembly and is typically tied off, for example, by a purse string suture. Thereafter, the anvil member is advanced toward the stapling assembly by rotation of a rotatable knob or wing nut assembly at the proximal end of the instrument. When proper approximation is achieved, the staples are expelled from the fastener assembly. A circular knife typically follows the application of the staples to excise unwanted tissue at the anastomosis site. The instrument is then removed from the lumen of the organ.

To a large degree, the recent explosion in laparoscopic surgical procedures may be attributed to the development of mechanical devices particularly adapted for use in a laparoscopic environment. For example, U.S. Pat. Nos. 5,084,057 and 5,100,520 to Green, et al. describe an endoscopic multiple clip applier which enabled the surgical community to fully realize the potential of endoscopic cholycystectomy. The Green '057 and '420 patents describe, inter alia, a gaseous seal means for obstructing the passage of gas from the insufflated body cavity.

Providing a sealing system for a circular anastomosis instrument is recognized in the art. The present invention provides a uniquely structured sealing system which not only effectively seals the instrument but is easy to manufacture and assemble and does not significantly increase the cost of the instrument.

SUMMARY OF THE INVENTION

The present invention provides a circular anastomosis instrument having means for preventing the flow of gas through the instrument during surgical procedures. Three seals are positioned within the body of the instrument to prevent/inhibit flow of gases through the instrument. A first seal is circumferentially positioned about the quill portion of the instrument and preferably permits the quill member to move relative to the seal. A second seal is disposed about apertures in the inner tube of the instrument. A third seal is located proximal of the second seal, is positioned about a portion of the anvil approximation mechanism of the instrument and is fabricated from polyethylene foam. The three seals, in combination, permit surgeons to perform a circular anastomosis while a portion of the patient's body is insufflated.

BRIEF DESCRIPTION OF THE DRAWINGS

The foregoing features of the present invention will become more readily apparent and may be understood by referring to the following detailed description of an illustrative embodiment of the surgical stapling apparatus and its sealing system, taking in conjunction with the accompanying drawings, in which.

DETAILED DESCRIPTION OF THE INVENTION

Figure 1:
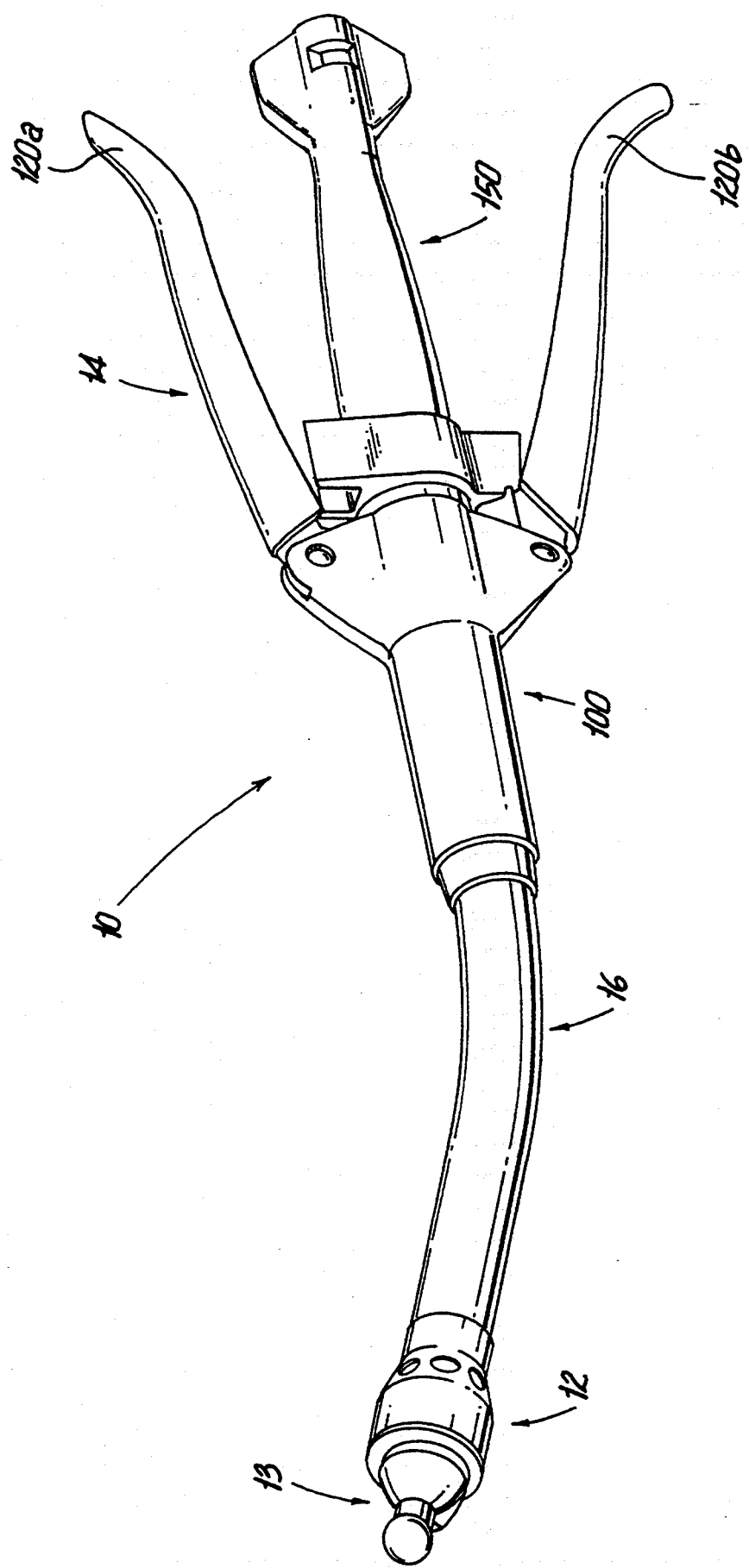
FIG. 1 is a perspective view of a surgical stapler incorporating a sealing system of the present invention.

An illustrative embodiment of a circular anastomosis surgical stapler 10, in which the sealing system of the present invention is incorporated, is generally shown in FIG. 1. A typical application of stapler 10 is connecting together two sections of hollow tubular body organ, (e.g., two intestinal sections) by means of applying an annular array of staples between the interiors of the organ sections. Stapler 10 includes distal stapling assembly 12, anvil member 13, proximal actuator assembly 14 and longitudinal shaft assembly 16 for connecting distal and proximal assemblies and for transmitting actuation forces and motions from the actuator assembly to the stapling assembly. Shaft assembly 16 can be straight or have a longitudinally curved portion as shown. In the particular embodiment shown in the drawing, this curved portion is an arc of a circle and therefore has a generally uniform radius along its length. Detailed descriptions and methods of using similar circular anastomosis devices are disclosed, for example, in commonly assigned U.S. Pat. Nos. 4,576,167, 5,005,749 and 5,119,983, which are incorporated herein by reference. Surgical stapler 10 can also be adapted to apply anastomosis rings and the like.

Figure 2:
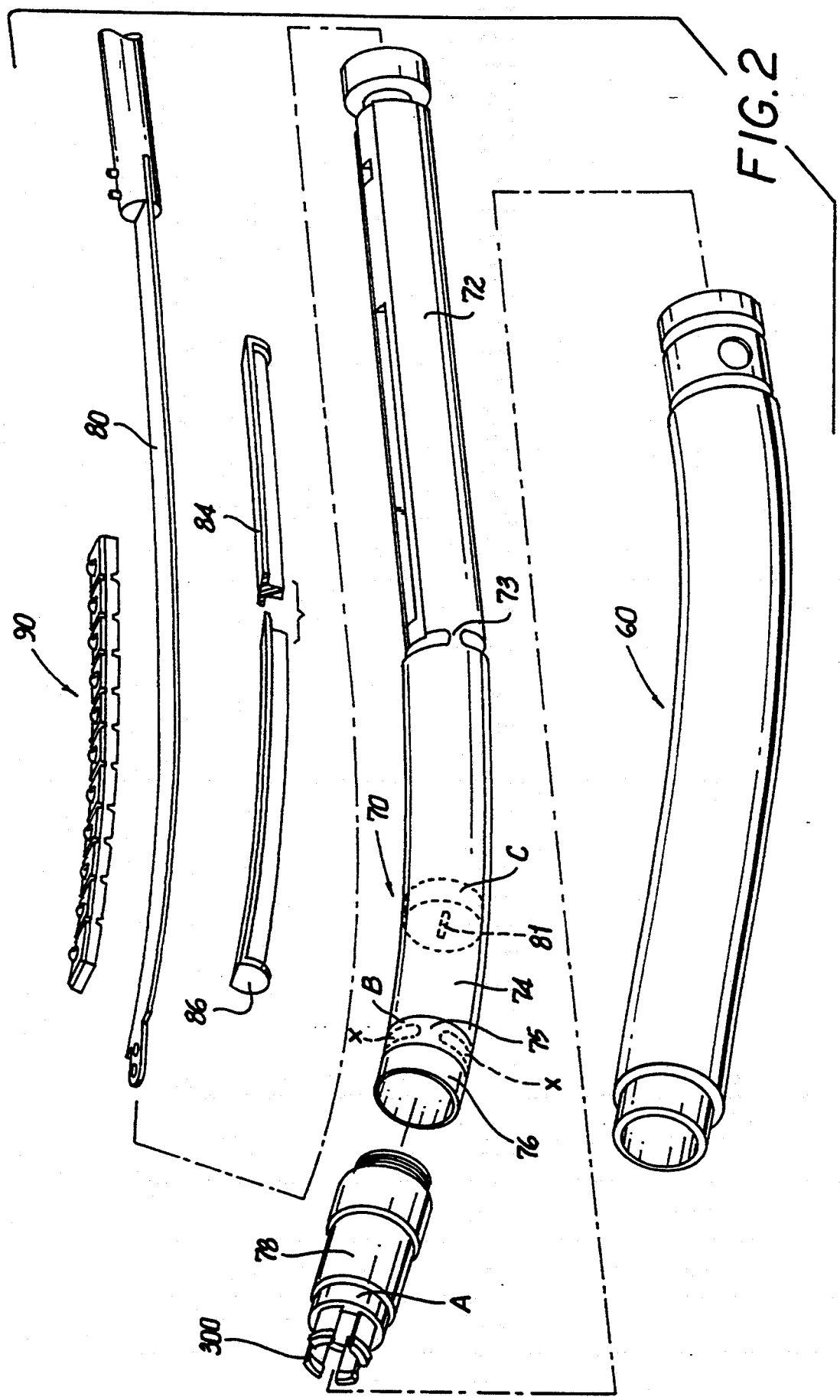
FIG. 2 illustrates an exploded perspective view of a portion of the apparatus of FIG. 1, showing the sealing system of the present invention.

With reference to FIGS. 1 and 2, the proximal end of outer shaft tube 60 is secured to housing 100. Inner tube 70 is disposed within outer shaft tube 60 and is mounted for longitudinal motion relative to tube 60. The distal end of inner tube 70 is threadably connected to extension tube 78 which is also longitudinally movable within outer tube 60. Tubes 70 and 78 constitute a compression member for transmitting a longitudinal compression force produced by operation of handles 120a and 120b of actuator assembly 14 and serve to transmit forces to stapling assembly 12. By squeezing handles 120a and 120b towards each other, tubes 70 and 78 are caused to move distally, thereby causing the ejection of staples, as is known in the art and described in detail in the above commonly assigned patents.

Tube 70 has a straight proximal portion 72, a curved intermediate portion 74, and distal portion 76. Sections 73 and 75 connect portions 72 and 74, and 74 and 76 respectively. Apertures X, adjacent sections 74, 75 and 76, allow some bending, thereby providing flexibility in tube 70. The material in sections 73 and 75 can be selected to yield when tube 70 is bent or flexed. The distal end of extension tube 78 includes quills 300 which extend into staple assembly 12 where the quills serve to contact staple pushers (not shown) to drive the staples into body tissue.

Turning to the sealing system of the present invention, with reference to FIG. 2, three seals are provided. A first seal A is disposed circumferentially about quills 300 where the quills engage the body portion of extension tube 78. The seal is positioned such that the inner portion of the seal engages the outer portion of the quill/tube engagement while the outer portion of the seal engages a portion of the interior of outer tube 60. The location of this first seal therefore inhibits flow of gases between extension tube 78 and outer tube 60. During operation, quills 300 can move relative to seal A. Seal A is preferably at least partially manufactured from a foam-type material, most preferably a polyethylene closed cell foam.

A second seal B is disposed circumferentially about section 75 and apertures X. This seal can be made from any suitable material which can prevent gases from flowing from the interior of tube 70 through apertures X. Suitable materials for this type of seal include heat shrinkable materials such as polyvinyl chloride which can be placed around section 75 and heated to provide a tight fit about apertures X. Other suitable materials include adhesive tapes. Seal B prevents gases from flowing through tubes 70 and 78 and out apertures X.

A third seal C (shown in phantom) is disposed within tube 70 and proximal of seal B. This seal is provided with longitudinal aperture 81 to allow band 80 to pass therethrough. Band 80 serves to transmit movement and tension forces from rotatable portion 150 of stapler 10 to anvil member 13, as is known in the art. Preferably, several bands 80 may be used in a stacked relationship, each passing through seal C at aperture 81. Seal C may be manufactured from similar materials as that of seal A and serves to prevent gases from passing through curved portion 74 of inner tube 70. Both seals A and C can further be provided with sufficient quantities of silicone grease to further facilitate sealing effectiveness.

In operation, when the instrument of the present invention is inserted into an insufflated peritoneum, (e.g., through a natural orifice in the body or through a surgically placed port, such as a cannula), seal A will prevent insufflation gases from passing between the exterior of tube 78 and the interior of outer tube 60; seal B will prevent gases from flowing out apertures X from the interior of tube 70; and seal C will prevent gases from flowing through the interior of tube 70.

It will be understood that the foregoing is only illustrative of the principles of the inventions and that various modifications can be made by those skilled in the art without departing from the scope and spirit of the invention.

What is claimed is:

1. A surgical instrument for performing a circular anastomosis comprising:

a shaft assembly having an inner compression member and an outer tube with proximal and distal end portions, the compression member having a plurality of quills at a distal end thereof;

a fastener assembly disposed at said outer tube distal end portion;

a housing portion disposed at said outer tube proximal end portion;

an anvil assembly disposed distal of said fastener assembly and means for manipulating said anvil assembly disposed proximal of housing portion, wherein at least one elongate member is disposed within said shaft assembly, said elongate member for transferring movement from said anvil manipulating means to said anvil;

an actuator assembly associated with said housing portion for manipulating said inner compression member; and a plurality of seals positioned within said shaft assembly for inhibiting the flow of gases therethrough, said plurality of seals including a first seal configured and dimensioned to at least partially contact an outer portion of said compression member and an inner portion of said outer tube, said first seal being at least partially disposed about the quills of said compression member, a second seal disposed about said compression member and located proximal of said first seal and a third seal disposed about said elongate member and located proximal of said second seal, said third seal fabricated from polyethylene foam.

2. The surgical instrument of claim 1, wherein said compression member is tubular in configuration.

3. The surgical instrument of claim 1, wherein said first seal is at least partially fabricated from polyethylene.

4. The surgical instrument of claim 1, wherein said second seal is at least partially fabricated from a material which deforms upon application of heat.

5. The surgical instrument of claim 1, wherein said second seal is an adhesive tape.

6. The surgical instrument of claim 1, wherein said third seal is at least partially fabricated from closed cell polyethylene foam.

* * * * *